(12) United States Patent
Mahboob

(10) Patent No.: US 12,605,423 B2
(45) Date of Patent: Apr. 21, 2026

(54) PEPTIDE INHIBITORS TARGETING METHYLTRANSFER MECHANISM OF SARS-COV-2

(71) Applicant: United Arab Emirates University, Al Ain (AE)

(72) Inventor: Abdulla Mahboob, Al Ain (AE)

(73) Assignee: United Arab Emirates University, Al Ain (AE)

( * ) Notice: Subject to any disclaimer, the term of this patent is extended or adjusted under 35 U.S.C. 154(b) by 0 days.

(21) Appl. No.: 17/469,491

(22) Filed: Sep. 8, 2021

(65) Prior Publication Data

US 2023/0074138 A1      Mar. 9, 2023

(51) Int. Cl.
*A61K 38/08*      (2019.01)
*A61K 47/64*      (2017.01)
*A61P 31/14*      (2006.01)

(52) U.S. Cl.
CPC .............. *A61K 38/08* (2013.01); *A61K 47/64* (2017.08); *A61K 47/645* (2017.08); *A61P 31/14* (2018.01)

(58) Field of Classification Search
CPC .............. C07K 14/005; C07K 2319/00; C07K 2319/70; C07K 14/165; C07K 16/10; A61K 2039/525; A61K 47/6911; A61P 31/14; A61P 31/12; G01N 2333/165
See application file for complete search history.

(56) References Cited

PUBLICATIONS

Ke et al. Short peptides derived from the interaction domain of SARS coronavirus nonstructural protein nsp10 can suppress the 2'-O-methyltransferase activity of nsp 10/nsp16 complex. Virus Research. 2012; 167: 322-328. (Year: 2012).*
Lugari et al. Molecular Mapping of the RNA Cap 2'-O Methyltransferase Activation Interface between Severe Acute Respiratory Syndrome Coronavirus nsp10 and nsp16. J Biol Chem. 2010; 285(43): 33230-33241. (Year: 2010).*
Zhang et al. Cysteine methylation disrupts ubiquitin-chain sensing in NF-kB activation. Nature. 2012; 481: 204-208. (Year: 2012).*
Wang et al. Coronavirus nsp10/nsp16 Methyltransferase Can Be Targeted by nsp10-Derived Peptide In Vitro and In Vivo To Reduce Replication and Pathogenesis. J Virol. 2015; 89:8416-8427. (Year: 2015).*
Ye et al. DepoFoamTM technology: a vehicle for controlled delivery of protein and peptide drugs. Journal of Controlled Release. 2000; 64: 155-166. (Year: 2000).*
Biosynthesis. N-Terminal Acetylation Amidation Peptides Chemically Synthesized Aminopeptidases Intracellular. https://www.biosyn.com/faq/why-acetylate-and-amidate-a-peptide.aspx Nov. 11, 2008. (Year: 2008).*
Ben Hu, "Characteristics of SARS-CoV-2 and COVID-19", Article, 2021, 141-154, vol. 19, Microbiology.
Savannah F. Pedersen, "SARS-CoV-2: a storm is raging", Journal, 2020, 2022-2205,vol. 130, No. 5, The Journal of Clinical Investigation.
Daolin Tang, "The hallmarks of COVID-19 disease", Article, 2020, 1-24, vol. 16, No. 5, Plos Pathogens.
Sufang Tian, "Pulmonary Pathology of Early-Phase 2019 Novel Coronavirus (COVID-19) Pneumonia in Two Patients With Lung Cancer", Article, 2020, 700-704, vol. 15, No. 5, Journal of Thoracic Oncology.
Petra Krafcikova, "Structural analysis of the SARS-CoV-2 methyltransferase complex involved in RNA cap creation bound to sinefungin", Article, 2020, 1-7, vol. 11, Nature Communcations.
S. K. Kritas, "Mast Cells Contribute to Coronavirus-Induced Inflammation: New Anti-Inflammatory Strategy", Journal, 2020, 9-14, vol. 31, No. 1, Journal of Biological Regulators & Homeostatic Agents.
Tao Liu, "The potential role of IL-6 in monitoring coronavirus disease 2019", Article, 2020, 1-23, No. 12, EMBO Molecular Medicine.
Guang Chen, "Clinical and immunological features of severe and moderate coronavirus disease 2019", Journal, 2020, 2620-2629, vol. 130, No. 5, Clinical Medicine—The Journal of Clinical Investigation.
Jurgen Scheller, "The pro- and anti-inflammatory properties of cytokine interleukin-6", Article, 2011, 878-888, vol. 1813, Biochimica et Biophysica Acta.
David Alex Cronkite, "The Regulation of Inflammation by Innate and Adaptive Lymphocytes", Article, 2018, 1-14, vol. 2018, Journal of Immunology Research.
Alberto Mantovani, "IL-1 and related cytokines in innate and adaptive immunity in health and disease", Article, 2019, 778-795, vol. 50, No. 4, Immunity.
Marcel F. Nold, "Interleukin 37 is a fundamental inhibitor of innate immunity", Article, 2010, 1014-1022, vol. 11, No. 11, Nature Immunology.
Haishan Lin, "Cloning and Characterization of IL-1HY2, a Novel Interleukin-1 Family Member*", Journal, 2001, 20597-20602, vol. 275, No. 23, The Journal of Biological Chemistry.
Yu Mei, "IL-37: An anti-inflammatory cytokine with antitumor functions", Article, 2018, 1-9, vol. 2, No. 2, Cancer Reports.
Gamal Allam, "The potential role of interleukin-37 in infectious diseases", Article, 2020, 3-10, vol. 39, No. 1, International Reviews of Immunology.
Ziyi Yang, "Role of IL-37 in Cardiovascular Disease Inflammation", Article, 2019, 923-930, vol. 35, Canadian Journal of Cardiology.

(Continued)

*Primary Examiner* — Li N Komatsu
*Assistant Examiner* — Jia-Hai Lee
(74) *Attorney, Agent, or Firm* — Hayes Soloway PC; Todd A. Sullivan; Colin Dean

(57) ABSTRACT

Synthetic peptides mimicking the nsp10 sequence in the region interacting with nsp16 capable of penetrating cell membranes and inhibiting SARS-CoV-2 replication for the treatment of moderate to severe COVID-19. The invention relates to peptides inhibiting SARS-CoV-2 replication, likely through inhibition of Methyltransferase complexes (NSP10/NSP16 and NSP10/NSP14). The peptide of the present invention, P3, contains sequences corresponding to amino acids 89-96 of the non-structural protein 10 (NSP10) of SARS-CoV-2, with the only Cysteine modified to a Methionine. This peptide was made based on two previous designs P1 and P2, which constituted the amino acids 68-96 of the NSP10 protein of SARS-CoV-2.

12 Claims, 4 Drawing Sheets

Specification includes a Sequence Listing.

(56) References Cited

PUBLICATIONS

Darrio Ummarino, "IL-38 promotes anti-inflammatory effects", Research Abstract, 2017, 1 pg., Nature Reviews | Rheumatology.

Wang-Dong Xu, "Role of interleukin-38 in Chronic inflammatory Diseases: A Comprehensive Review", Article, 2018, 1--6, vol. 9, No. 1462, Frontiers in Immunology.

Lihui Xie, "IL-38: A New Player in Inflammatory Autoimmune Disorders", Article, 2019, 1-22, vol. 9, No. 345, Biomolecules.

P. Conti, "How To Reduce the Likelihood of Coronavirus-19 (CoV-19 or SARS-CoV-2) Infection and Lung Inflammation Mediated By IL-1", Journal, 2020, 33-338, vol. 34, No. 2, Journal of Biological Regulators & Homeostatic Agents.

Ang Li, "Correlation Between Early Plasma Interleukin 37 Responses With Low Inflammatory Cytokine Levels and Benign Clinical Outcomes in Severe Acute Respiratory Syndrome Coronavirus 2 Infection", Journal, 2021, 568-580, vol. 223, The Journal of Infectious Diseases.

Mar Masia, "Impact of interleukin-6 blockade with tocilizumab on SARS-CoV-2 viral kinetics and antibody responses in patients with COVID-19: A prospective cohort study", Research Paper, 2020, 1-9, vol. 60, EBioMedicine.

Yi Wang, "Coronavirus nsp10/nsp16 Methyltransferase Can Be Targeted by nsp10-Derived Peptide In Vitro and In Vivo To Reduce Replication and Pathogenesis", Journal, 2015, 8416-8427, vol. 89, No. 16, Journal of Virology.

Min Ke, "Short peptides derived from the interaction domain of SARS coronavirus nonstructural protein nsp10 can suppress the 2-O-methyltransferase activity of nsp10/nsp16 complex", Article, 2012, 322-328, vol. 167, Virus Research.

David E. Gordon, "A SARS-CoV-2 protein interaction map reveals targets for drug repurposing", Research Paper, 2020, 459-488, vol. 583, Nature.

Valeria Cagno, "SARS-CoV-2 cellular tropism", Comment on Research, 2020, 1-3, vol. 1, The Lancet.

Mohammad Y. Ansari, "Genetic inactivation of ZCCHC6 suppresses IL-6 expression and reduces the severity of experimental osteoarthritis in mice", Article, 2019, 583-593, vol. 71, No. 4, Arthritis Rheumatology.

Jingjiao Li, "Virus-Host Interactome and Proteomic Survey Reveal Potential Virulence Factors Influencing SARS-CoV-2 Pathogenesis", Article, 2021, 99-112, vol. 2, Med.

Kishan K. Nyati, "TLR4-induced NF-kB and MAPK signaling regulate the IL-6 mRNA stabilizing protein Arid5a", Article, 2017, 2687-2703, vol. 45, No. 5, Nucleic Acids Research.

Simone Criistina Soares Brandao, "Is Toll-like receptor 4 involved in the severity of COVID-19 pathology in patients with cardiometabolic comorbidities?", Journal, 2021, 102-110, vol. 58, Cytokine and Growth Factor Reviews.

Allison L. Tortura, "Toll-Like Receptor 3 Signaling via TRIF Contributes to a Protective Innate Immune Response to Severe Acute Respiratory Syndrome Coronavirus Infection", Article, 2015, 1-14, vol. 6, No. 3, MBio.

Frank L. Van De Veerdonk, "IL-38 binds to the IL-36 receptor and has biological effects on immune cells similar to IL-36 receptor antagonist", Article, 2012, 3001-3005, vol. 109, No. 8, PNAS.

Javier Mora, "Interleukin-38 is released from apoptotic cells to limit inflammatory macrophage responses", Article, 2016, 426-438, vol. 8, No. 5, Journal of Molecular Cell Biology.

X. L. Yuan, "Production of Recombinant Human Interleukin-38 and Its Inhibitory Effect on the Expression of Proinflammatory Cytokines in THP-1 Cells", Article, 2016, 466-473, vol. 50, No. 3, Molecular Cell Biology.

Haichao Yu, "IL-38 alleviates the inflammatory response and the degeneration of nucleus pulposus cells via inhibition of the NF-kB signaling pathway in vitro", Journal, 2020, 1-9, vol. 85, International Immunophamacology.

Ana-Maria Bulau, "Role of caspase-1 in nuclear translocation of IL-37, release of the cytokine, and IL-37 inhibition of innate immune responses", Article, 2014, 1-6, vol. 111, No. 7, PNAS.

Sheetal Sharma, "The IL-1 Family Member 7b Translocates to the Nucleus and Down-Regulates Proinflammatory Cytokines", Journal, 2008, 5477-5482, vol. 180 No. 8, The Journal of Immunology.

\* cited by examiner

```
                                                                              :**** *;****.:
SARS-COV     AGNATEVPANSTVLSFCAFAVDPAKAYKDYLASGGQPITNCVKMLCTHTGTGQAITVTPEANMDQESFGGASCCLYCRCH   80
SARS-COV-2   AGNATEVPANSTVLSFCAFAVDAAKAYKDYLASGGQPITNCVKMLCTHTGTGQAITVTPEANMDQESFGGASCCLYCRCH   80
MHV          --------------------------------------------------------------YGGASVCIYCRSR       13
MERS         AGSNTEFASNSSVLSLVNFTVDPQKAYLDFVNAGGAPLTNCVKMLTPKTGTGIAISVKPESTADQETYGGASVCLYCRAH   80
             1.......10........20........30........40........50........60........70........80

::**: .*.*. :**:
SARS-COV     IDHPNPKGFCDLKGKYVQIPTTCANDPVGFTLRNTVCTVCGMWKGYGCSCDQLREPLMQ-   139
SARS-COV-2   IDHPNPKGFCDLKGKYVQIPTTCANDPVGFTLKNTVCTVCGMWKGYGCSCDQLREPMLQ-   139
MHV          VEHPDVDGLCKLRGKF                                              29
MERS         IEHPDVSGVCKYKGKFVQIPAQCVRDPVGFCLSNTPCNVCQYWIGYGCNCDSLRQAALPQ   140
             .........90.......100.......110.......120.......130.......140
```

FIG. 1

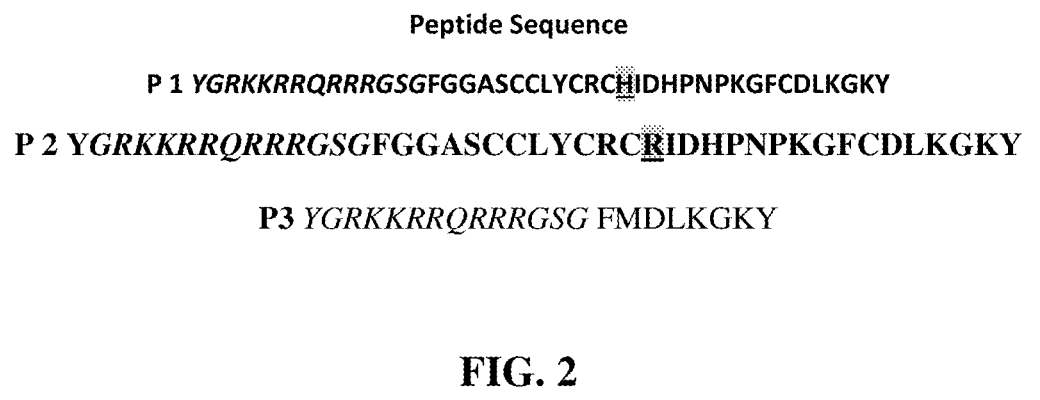

Peptide Sequence

P 1 *YGRKKRRQRRRGSG*FGGASCCLYCRCHIDHPNPKGFCDLKGKY

P 2 YG*RKKRRQRRRGSG*FGGASCCLYCRCRIDHPNPKGFCDLKGKY

P3 *YGRKKRRQRRRGSG* FMDLKGKY

FIG. 2

SEQUENCE LISTING

```
<160> NUMBER OF SEQ ID NOS: 17

<210> SEQ ID NO 1
<211> LENGTH: 8
<212> TYPE: PRT
<213> ORGANISM: Artificial Sequence
<220> FEATURE:
<223> OTHER INFORMATION: Synthetic Amino acid sequence

<400> SEQUENCE: 1

Phe Met Asp Leu Lys Gly Lys Tyr
1               5

<210> SEQ ID NO 2
<211> LENGTH: 22
<212> TYPE: PRT
<213> ORGANISM: Artificial Sequence
<220> FEATURE:
<223> OTHER INFORMATION: Synthetic Amino acid sequence

<400> SEQUENCE: 2

Tyr Gly Arg Lys Lys Arg Arg Gln Arg Arg Arg Gly Ser Gly Phe Met
1               5                   10                  15

Asp Leu Lys Gly Lys Tyr
            20

<210> SEQ ID NO 3
<211> LENGTH: 16
<212> TYPE: PRT
<213> ORGANISM: Artificial Sequence
<220> FEATURE:
<223> OTHER INFORMATION: Synthetic Amino acid sequence

<400> SEQUENCE: 3

Arg Arg Arg Arg Arg Arg Arg Arg Phe Met Asp Leu Lys Gly Lys Tyr
1               5                   10                  15

<210> SEQ ID NO 4
<211> LENGTH: 18
<212> TYPE: PRT
<213> ORGANISM: Artificial Sequence
<220> FEATURE:
<223> OTHER INFORMATION: Synthetic Amino acid sequence

<400> SEQUENCE: 4

Cys Arg Arg Arg Arg Arg Arg Arg Arg Cys Phe Met Asp Leu Lys Gly
1               5                   10                  15

Lys Tyr

<210> SEQ ID NO 5
<211> LENGTH: 20
```

```
<212> TYPE: DNA
<213> ORGANISM: Artificial Sequence
<220> FEATURE:
<223> OTHER INFORMATION: Variant Nucleotide Sequence

<400> SEQUENCE: 5
ccaagtacct ccaccagcat                                          20

<210> SEQ ID NO 6
<211> LENGTH: 20
<212> TYPE: DNA
<213> ORGANISM: Artificial Sequence
<220> FEATURE:
<223> OTHER INFORMATION: Variant Nucleotide Sequence

<400> SEQUENCE: 6
gggagttggc cagtaaatca                                          20

<210> SEQ ID NO 7
<211> LENGTH: 20
<212> TYPE: DNA
<213> ORGANISM: Artificial Sequence
<220> FEATURE:
<223> OTHER INFORMATION: Variant Nucleotide Sequence

<400> SEQUENCE: 7
cttggagttg gcccatagaa                                          20

<210> SEQ ID NO 8
<211> LENGTH: 20
<212> TYPE: DNA
<213> ORGANISM: Artificial Sequence
<220> FEATURE:
<223> OTHER INFORMATION: Synthetic Artificial Nucleotide Sequence

<400> SEQUENCE: 8
tggtgccaca atctgttgtt                                          20

<210> SEQ ID NO 9
<211> LENGTH: 20
<212> TYPE: DNA
<213> ORGANISM: Artificial Sequence
<220> FEATURE:
<223> OTHER INFORMATION: Variant Nucleotide Sequence

<400> SEQUENCE: 9
gctcctgctc ctgaaatgac                                          20

<210> SEQ ID NO 10
<211> LENGTH: 20
<212> TYPE: DNA
<213> ORGANISM: Artificial Sequence
<220> FEATURE:
<223> OTHER INFORMATION: Variant Nucleotide Sequence

<400> SEQUENCE: 10
ctggagcaat tggtgaggtt                                          20

<210> SEQ ID NO 11
<211> LENGTH: 20
<212> TYPE: DNA
<213> ORGANISM: Artificial Sequence
<220> FEATURE:
<223> OTHER INFORMATION: Variant Nucleotide Sequence

<400> SEQUENCE: 11
```
accaccacta ccaccaccac                                                   20

<210> SEQ ID NO 12
<211> LENGTH: 20
<212> TYPE: DNA
<213> ORGANISM: Artificial Sequence
<220> FEATURE:
<223> OTHER INFORMATION: Variant Nucleotide Sequence

<400> SEQUENCE: 12
tatccccatt tccaagtcca                                                   20

<210> SEQ ID NO 13
<211> LENGTH: 20
<212> TYPE: DNA
<213> ORGANISM: Artificial Sequence
<220> FEATURE:
<223> OTHER INFORMATION: Variant Nucleotide Sequence

<400> SEQUENCE: 13
cacgacggag tttcacaaga                                                   20

<210> SEQ ID NO 14
<211> LENGTH: 20
<212> TYPE: DNA
<213> ORGANISM: Artificial Sequence
<220> FEATURE:
<223> OTHER INFORMATION: Variant Nucleotide Sequence

<400> SEQUENCE: 14
cgatggaagt ttgaggcaat                                                   20

<210> SEQ ID NO 15
<211> LENGTH: 14
<212> TYPE: PRT
<213> ORGANISM: Artificial Sequence
<220> FEATURE:
<223> OTHER INFORMATION: Synthetic Amino acid sequence

<400> SEQUENCE: 15

Tyr Gly Arg Lys Lys Arg Arg Gln Arg Arg Arg Gly Ser Gly
1               5                   10

<210> SEQ ID NO 16
<211> LENGTH: 8
<212> TYPE: PRT
<213> ORGANISM: Artificial Sequence
<220> FEATURE:
<223> OTHER INFORMATION: Synthetic Amino acid sequence

<400> SEQUENCE: 16

Arg Arg Arg Arg Arg Arg Arg Arg
1               5

<210> SEQ ID NO 17
<211> LENGTH: 10
<212> TYPE: PRT
<213> ORGANISM: Artificial Sequence
<220> FEATURE:
<223> OTHER INFORMATION: Synthetic Amino acid sequence

<400> SEQUENCE: 17

Cys Arg Arg Arg Arg Arg Arg Arg Arg Cys
1               5                   10

PEPTIDE INHIBITORS TARGETING METHYLTRANSFER MECHANISM OF SARS-COV-2

TECHNICAL FIELD

The present invention relates to peptide inhibitors against the casative agent of COVID-19 (SARS-CoV-2 virus).

REFERENCE MATERIALS

Various sequence listings and variant listings are provided herein and attached in a separate sequence listing .txt file. The provide listings are incorporated herein by reference

BACKGROUND OF THE INVENTION

Severe Acute Respiratory Syndrome Coronavirus 2 (SARS-CoV-2) is a highly transmissible pathogenic coronavirus. It is responsible for the coronavirus disease 2019 (COVID-19) pandemic, resulting in threats to human health worldwide. The illness caused by SARS-CoV-2 could vary from mild flu-like symptoms to severe respiratory failure [1].

Among the molecular strategies to target SARS-CoV-2, protein-protein interactions, particularly those responsible for evasion of host defenses, represent a very attractive target. One such protein-protein interaction concerns the mechanism of RNA methylation used by Coronaviruses to imitate the host's RNA as a defense against degradation by Interferons. The Methylation involves two steps, a 2'-O-Methylation, and a N7-Methylation both occurring at the cap of the nascent RNA. While 2'-O-Methylation occurs via the non-structural protein 16 (NSP16), the N7 Methylation occurs through the non-structural protein 14 (NSP14).

The nsp10 protein in coronaviruses is known to constitute a cofactor in the methyltransferase complexes it forms with NSP14 and NSP16 [1]. The crystal structure of the NSP10/NSP16 complex of SARS-CoV-2 was solved early on during the pandemic [2], giving insight into the binding and interaction interface of NSP10/NSP16.

Development of efficient therapies for COVID-19 is the current focus of intense scientific and medical research. With the newly emerging variants of the SARS-CoV-2 virus displaying resistance towards neutralizing antibodies, hence threatening the efficacy of vaccines[3][3], alternative therapeutic approaches are in urgent need.

SUMMARY OF THE EMBODIMENTS

The invention relates to peptides inhibiting SARS-CoV-2 replication, likely through inhibition of Methyltransferase complexes (NSP10/NSP16 and NSP10/NSP14). The peptide of the present invention, P3, contains sequences corresponding to amino acids 89-96 of the non-structural protein 10 (NSP10) of SARS-CoV-2, with the only Cysteine modified to a Methionine. This peptide was made based on two previous designs P1 and P2, which constituted the amino acids 68-96 of the NSP10 protein of SARS-CoV-2. Our studies have indicated that P1 is a highly toxic peptide with a 50% cytotoxicity seen at 1 μg/mL. ($CC_{50}$ 1 μg/mL), likely due to its simulation of the pro-inflammatory Interleukin-6 (IL-6 protein), while P2 contains the same sequence as P1 but having an amino acid mutation from Histidine to Arginine has no detectable activity against SARS-CoV-2.

The SARS-CoV-2 Methyltransferase enzyme formed by the non-structural protein 10 (NSP10) and non-structural protein 16 (NSP16) is essential for the virus' evasion of host defenses by protecting the viral RNA from interferon response. P1 has high toxicity and stimulates an inflammatory pathway. P1 contains a Zinc "knuckle" motif known to stimulate IL-6 inflammation response in other studies. Using computational methods we developed P3 to be a shorter peptide lacking the Zinc knuckle that interacts with NSP16, and has a 90% Effective Concentration of 3.3 μM ($EC_{90}$ 3.3 μM).

Generally, there are several advantages in using peptide inhibitors when compared to small molecules. The most relevant being the streamlined method of synthesis and the decreased likelihood of resistance arising as peptides bind to a larger portion of the receptor. More specifically, the treatment targets the Methyltransferase portion of the virus. This enzyme is very conserved among strains and hence this treatment is likely to be effective against emerging strains that evade antibody recognition. So far, no disadvantages appeared.

Disclosed herein is a peptide mimicking the NSP10 sequence in the region interacting with NSP16 capable of penetrating cell membranes and inhibiting SARS-CoV-2 replication and compositions containing these peptides. With possibly similar effects against other Coronaviruses.

In a first embodiment, disclosed herein is an eight amino acids peptide according to amino acid sequence FCDLKGKY, which corresponds to amino acids 89 to 96 of the NSP10 sequence in SARS-CoV-2, with a Cysteine modified to Methionine FMDLKGKY (P3) (SEQ ID NO: 1) or a subset of the P3 sequence.

In a second embodiment, P3 comprises a peptide sequence from the HIV Tat to allow penetration of cell membrane. The HIV Tat sequence may be substituted by any other suitable peptide sequences accessible to a person of ordinary skill in the art that allows penetration of the cell membrane.

In a third embodiment, a peptide sequence linked to P3 comprises a 14 amino acid sequence from the HIV Tat peptide sequence, or by any other suitable peptide sequences accessible to a person of ordinary skill in the art that allows penetration of the cell membrane In a fourth embodiment, the HIV Tat peptide sequence is YGRKKRRQRRRGSG (SEQ ID NO: 15).

In a preferred embodiment of the present disclosure, a peptide sequence linked to P3 comprises amino acid sequence YGRKKRRQRRRGSGFMDLKGKY (SEQ ID NO: 2).

In another embodiment, P3 is linked to a shorter sequence of eight Arginine residues (R8), RRRRRRRR FMDLKGKY (SEQ ID NO: 3) or the cyclized equivalent thereof, C*RRRRRRRRC*FMDLKGKY (SEQ ID NO: 4), where C* indicates a cyclized cysteine residue.

In certain embodiments, herein provided is a pharmaceutical composition comprising a therapeutically effective amount of a peptide of sequence P3, comprising a cell-penetrating peptide amino acid sequence, such as from the HIV Tat peptide sequence or the R8 sequence and variations thereof, and a pharmaceutically acceptable carrier for delivery to a subject.

In further embodiments, the HIV Tat peptide sequence comprises the peptide sequence YGRKKRRQRRRGSG (SEQ ID NO: 15) and the R8 sequence comprises RRRRRRRR (SEQ ID NO: 16) or the cyclized variation of R8 (cR8) C*RRRRRRRRC* (SEQ ID NO: 17).

In certain embodiments, disclosed is a method of treating a subject afflicted by SARS-CoV-2, the method comprising administering to the subject in need thereof a therapeutically effective amount of the peptide of sequence P3, comprising a cell-penetrating sequence such as shown above, and a pharmaceutically acceptable carrier for delivery to a subject.

BRIEF DESCRIPTION OF THE FIGURES

FIG. 1. illustrates alignment of the NSP10-derived sequence employed to inhibit the replication of Murine Hepatitis Virus (MHV) with full length NSP10 sequences from SARS-CoV, SARS-CoV-2, and MERS-CoV. The red box indicates a Proline to Valine substitution found in MHV and MERS-CoV but not in SARS-CoV and SARS-CoV-2.

FIG. 2 illustrates amino acids sequences of Peptides P1, P2, and P3 derived from the NSP10 protein of SARS-CoV-2 interacting with NSP16. Italics indicate amino acids of HIV-Tat sequence. Bold and underlined letters indicate substitution of Histidine with Arginine at position 26 (H26R).

DETAILED DESCRIPTION OF SPECIFIC EMBODIMENTS

A study was conducted to identify novel peptides for inhibiting SARS-CoV-2 replication, preferably through inhibition of Methyltransferase complexes. Peptides, P1 and P2 are derived from the SARS-CoV-2's NSP10 protein region that forms the interaction surface with NSP16 were designed. P1 constituted sequence identical to NSP10's amino acids 68-96 of SARS-CoV-2, while in P2 we altered the binding capacity by introducing one amino acid substitution, Histidine to Arginine (H80R in accordance with NSP10 numbering), relying on recently available X-ray structural data [5]. Both peptides were designed with an N-terminal 14 amino acid sequence corresponding to the protein transduction domain of the HIV's Trans-Activator of Transcription (TAT) protein to allow penetration of the cell membrane.

Figure 3:
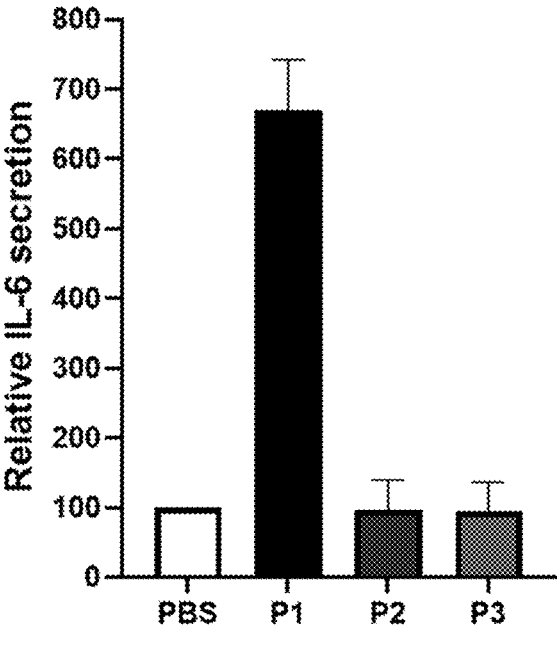
FIG. 3 The IL-6 stimulation caused by the peptides P1, P2, and P3 compared to Phosphate-buffered saline (PBS) as negative control. IL-6 levels are shown in relative units as measured through an Enzyme-linked Immunosorbent Assay (ELISA). 10 μM of each peptide was added.

Treatment with P1 on cultured human cells strongly increased IL-6 secretion by the human non-small cell lung cancer cell line NCIH1792, and revealed profound cytotoxic activity on Caco-2 human colorectal adenocarcinoma cells. In contrast, treatment with P2, which harbors the mutation H80R, displayed no IL-6 induction and no cytotoxicity as reported in a recently submitted publication by our group. We hypothesized that the source of this cytotoxicity of P1 is the Zinc "knuckle" motif found in the sequence. This is particularly supported by evidence that P2 possesses no cytotoxicity and no binding due to the H80R mutation making the binding of Zinc atom at the Zinc knuckle unfavourable according to Multiconformer Continuum Electrostatics (MCCE) calculations. So, in conclusion, our previous work indicated that: (1) the Zinc "knuckle" is the likely source of cytotoxicity (2) this cytotoxicity at least partly originates from an overstimulation of IL-6 proinflammatory cytokine (3) removal of the Zinc knuckle causes a loss of binding. FIG. 3 shows the IL-6 stimulation in NCIH1792 resulting from application of 10 μM of the respective peptide.

Based on our previous results described above, we aimed to develop a non-toxic peptide that is also capable of reducing replication of SARS-CoV-2. Towards that goal, we conducted Molecular Mechanics-Poisson Boltzmann Surface Area (MM-PBSA) simulations on the NSP10/NSP16 complex to divide the binding into components from each amino acid. Based on the results, eight amino acids that appear in sequence contribute significantly to the favourable binding between NSP10 and NSP16. These amino acids happen to be within the P1 and P2 sequences; however, they are not part of the Zinc "knuckle" motif that we have previously hypothesized is responsible for the IL-6 induction. Table 1 below shows the raw data from the MM-PBSA simulation indicating each amino acid's contribution to the binding.

TABLE 1

Amino acids contribution to the binding energy
between NSP10 and NSP16 (amino acids from NSP10 are shown).
Energy is decomposed into Solvation, None-Polar and Total.
The amino acids making up the P3 pepide sequence are
highlighted in yellow (amino acids 89 to 96 of NSP10).

| Residue | Location | Internal | Solvation | Non-Polar | TOTAL |
|---|---|---|---|---|---|
| ALA | 18 | L | -0.00385 | 0.003598263 | -10.96084 |
| PHE | 19 | L | -0.008655 | 0.007524359 | 0.330395 |
| ALA | 20 | L | -0.00217 | 0.001122987 | -0.13272 |
| VAL | 21 | L | -0.002995 | 0.000724552 | 0.66007 |
| ASP | 22 | L | -0.004515 | 0.001029454 | 8.15778 |
| ALA | 23 | L | -0.00659 | 0.001171281 | -0.35762 |
| ALA | 24 | L | -0.00444 | 0.000816333 | -0.11414 |

TABLE 1-continued

Amino acids contribution to the binding energy
between NSP10 and NSP16 (amino acids from NSP10 are shown).
Energy is decomposed into Solvation, None-Polar and Total.
The amino acids making up the P3 pepide sequence are
highlighted in yellow (amino acids 89 to 96 of NSP10).

| Residue | Location | Internal | Solvation | Non-Polar | TOTAL |
|---|---|---|---|---|---|
| LYS | 25 | L | -0.0034 | 0.000547723 | -4.39762 |
| ALA | 26 | L | -0.003385 | 0.000544771 | -0.41138 |
| TYR | 27 | L | -0.019275 | 0.001949199 | 0.03235 |
| LYS | 28 | L | -0.004605 | 0.000615609 | -3.56562 |
| ASP | 29 | L | -0.00249 | 0.000529056 | 4.442335 |
| TYR | 30 | L | -0.012295 | 0.003173007 | -0.415835 |
| LEU | 31 | L | -0.006825 | 0.000924324 | -0.33809 |
| ALA | 32 | L | -0.00143 | 0.000495076 | -0.244495 |
| SER | 33 | L | -0.00164 | 0.000548088 | 0.055 |
| GLY | 34 | L | -0.002085 | 0.000661646 | 0.18102 |
| GLY | 35 | L | -0.00322 | 0.000813388 | -0.55759 |
| GLN | 36 | L | -0.012355 | 0.002338584 | 0.55003 |
| PRO | 37 | L | -0.01976 | 0.002638636 | 0.030155 |
| ILE | 38 | L | -0.118495 | 0.020193563 | -1.731285 |
| THR | 39 | L | -0.278055 | 0.048696016 | 3.1806 |
| ASN | 40 | L | -2.91269 | 0.467878087 | -4.22589 |
| CYS | 41 | L | -0.595035 | 0.125623381 | -1.945755 |
| VAL | 42 | L | -3.588745 | 0.37603553 | 1.025445 |
| LYS | 43 | L | -3.131435 | 0.592256596 | 10.8787 |
| MET | 44 | L | -3.980605 | 0.390054521 | -1.571945 |
| LEU | 45 | L | -6.19448 | 0.745462534 | -2.31204 |
| CYS | 46 | L | -1.386995 | 0.323567049 | 0.267555 |
| THR | 47 | L | -1.698645 | 0.378707168 | 0.36481 |
| HIP | 48 | L | -0.317665 | 0.096229064 | 16.76558 |
| THR | 49 | L | -0.127865 | 0.036245921 | -0.17708 |
| GLY | 50 | L | -0.03316 | 0.005781384 | -0.101165 |
| THR | 51 | L | -0.024365 | 0.00292092 | 0.555555 |
| GLY | 52 | L | -0.010785 | 0.00092129 | 0.32198 |
| GLN | 53 | L | -0.022725 | 0.002406112 | -0.01873 |
| ALA | 54 | L | -0.01444 | 0.000816333 | 0.332425 |
| ILE | 55 | L | -0.04945 | 0.004012169 | -0.9625 |
| THR | 56 | L | -0.111915 | 0.010199891 | 2.31606 |
| VAL | 57 | L | -1.009755 | 0.252807446 | 1.21621 |
| THR | 58 | L | -1.03321 | 0.210623422 | -0.44678 |
| PRO | 59 | L | -1.264605 | 0.324721433 | -1.634115 |
| GLU | 60 | L | -0.136355 | 0.017256563 | -14.087795 |

TABLE 1-continued

Amino acids contribution to the binding energy
between NSP10 and NSP16 (amino acids from NSP10 are shown).
Energy is decomposed into Solvation, None-Polar and Total.
The amino acids making up the P3 pepide sequence are
highlighted in yellow (amino acids 89 to 96 of NSP10).

| Residue | Location | Internal | Solvation | Non-Polar | TOTAL |
|---|---|---|---|---|---|
| ALA | 61 | L | −0.05787 | 0.005662429 | −0.65451 |
| ASN | 62 | L | −0.030645 | 0.003011474 | −0.51051 |
| MET | 63 | L | −0.026995 | 0.004979455 | −0.466035 |
| ASP | 64 | L | −0.020015 | 0.004839915 | −12.745375 |
| GLN | 65 | L | −0.04819 | 0.008558265 | −1.29514 |
| GLU | 66 | L | −0.51664 | 0.305638676 | −18.028895 |
| SER | 67 | L | −0.202695 | 0.016804225 | −1.638165 |
| PHE | 68 | L | −0.39341 | 0.030626 | −0.43583 |
| GLY | 69 | L | −0.79011 | 0.102335028 | −3.61574 |
| GLY | 70 | L | −0.777975 | 0.126718603 | −4.09283 |
| ALA | 71 | L | −1.87421 | 0.579294982 | −5.899805 |
| SER | 72 | L | −1.384595 | 0.201339194 | −3.962375 |
| CYS | 73 | L | −0.19086 | 0.017810963 | −2.515275 |
| CY3 | 74 | L | −0.25328 | 0.41064609 | −39.25236 |
| LEU | 75 | L | −0.06864 | 0.008356459 | 1.56628 |
| TYR | 76 | L | −0.096485 | 0.010022962 | 1.062975 |
| CY3 | 77 | L | −1.08281 | 0.491515233 | −32.233995 |
| ARG | 78 | L | −2.266645 | 0.367158071 | −21.68491 |
| CYS | 79 | L | −0.15372 | 0.032888016 | −0.31092 |
| HIP | 80 | L | −1.334495 | 0.783144157 | −61.360025 |
| ILE | 81 | L | −0.08497 | 0.039144592 | 0.923395 |
| ASP | 82 | L | −0.056645 | 0.045544582 | 21.91706 |
| HD1 | 83 | L | −2.3837 | 1.800560152 | −41.10589 |
| PRO | 84 | L | −0.010395 | 0.001363442 | −0.38437 |
| ASN | 85 | L | −0.013015 | 0.001828873 | 0.937135 |
| PRO | 86 | L | −0.00815 | 0.001548386 | 0.531235 |
| LYS | 87 | L | −0.02483 | 0.008167074 | −6.40445 |
| GLY | 88 | L | −0.016505 | 0.004049688 | 1.24586 |
| PHE | 89 | L | −0.15167 | 0.081621327 | −1.41066 |
| CYS | 90 | L | −0.521295 | 0.667780943 | −41.250655 |
| ASP | 91 | L | −0.070405 | 0.022848216 | 6.024405 |
| LEU | 92 | L | −0.3307 | 0.056110249 | 1.038685 |
| LYS | 93 | L | −2.727905 | 0.781566207 | −56.38669 |
| GLY | 94 | L | −1.696965 | 0.596138729 | −7.81124 |
| LYS | 95 | L | −0.99218 | 0.171729431 | −2.35117 |
| TYR | 96 | L | −2.275405 | 0.676204141 | −3.91126 |

TABLE 1-continued

Amino acids contribution to the binding energy
between NSP10 and NSP16 (amino acids from NSP10 are shown).
Energy is decomposed into Solvation, None-Polar and Total.
The amino acids making up the P3 pepide sequence are
highlighted in yellow (amino acids 89 to 96 of NSP10).

| Residue | Location | Internal | Solvation | Non-Polar | TOTAL |
|---|---|---|---|---|---|
| VAL | 97 | L | −0.092195 | 0.005821252 | −0.05095 |
| GLN | 98 | L | −0.06561 | 0.003848103 | 0.917845 |
| ILE | 99 | L | −0.044665 | 0.004442159 | −0.606465 |
| PRO | 100 | L | −0.02032 | 0.004434817 | 0.296505 |
| THR | 101 | L | −0.093815 | 0.095067349 | 0.23469 |
| THR | 102 | L | −0.018815 | 0.009863102 | 0.280155 |
| CYS | 103 | L | −0.017325 | 0.004209439 | 0.806935 |
| ALA | 104 | L | −0.06901 | 0.025823437 | 0.87126 |
| ASN | 105 | L | −0.049795 | 0.015256572 | 0.78225 |
| ASP | 106 | L | −0.02634 | 0.003479138 | 0.92431 |
| PRO | 107 | L | −0.054515 | 0.005509971 | −0.09719 |
| VAL | 108 | L | −0.04171 | 0.005203451 | −0.219695 |
| GLY | 109 | L | −0.006535 | 0.000573389 | 0.236195 |
| PHE | 110 | L | −0.01591 | 0.001184019 | −0.045605 |
| THR | 111 | L | −0.017265 | 0.001778981 | 0.353835 |
| LEU | 112 | L | −0.01038 | 0.001302152 | −0.082745 |
| LYS | 113 | L | −0.005145 | 0.000744295 | 1.416935 |
| ASN | 114 | L | −0.00533 | 0.000539537 | 0.15133 |
| THR | 115 | L | −0.003895 | 0.000503959 | −0.50744 |
| VAL | 116 | L | −0.006855 | 0.000744295 | 0.172435 |
| CY1 | 117 | L | 0.199385 | 0.306704054 | −60.323715 |
| THR | 118 | L | −0.002745 | 0.000509877 | −0.19039 |
| VAL | 119 | L | −0.002445 | 0.000506927 | −0.23466 |
| CY1 | 120 | L | 0.253735 | 0.28360193 | −62.359095 |
| GLY | 121 | L | −0.00395 | 0.000507445 | −0.01696 |
| MET | 122 | L | −0.007875 | 0.000623999 | 0.31769 |
| TRP | 123 | L | −0.0169 | 0.000842615 | −0.28007 |
| LYS | 124 | L | −0.003125 | 0.000386491 | 2.82385 |
| GLY | 125 | L | −0.001415 | 0.000492722 | −0.16342 |
| TYR | 126 | L | −0.00705 | 0.000739932 | −0.003315 |
| GLY | 127 | L | −0.00203 | 0.000359305 | −0.27974 |
| CY1 | 128 | L | 0.37774 | 0.216564176 | −60.69941 |
| SER | 129 | L | −0.00134 | 0.000473709 | −0.026485 |
| CY1 | 130 | L | 0.260755 | 0.275505163 | −59.425885 |
| ASP | 131 | L | −0.000765 | 0.000423999 | −5.19916 |
| GLN | 132 | L | −0.001075 | 0.000359687 | −0.092215 |

TABLE 1-continued

Amino acids contribution to the binding energy
between NSP10 and NSP16 (amino acids from NSP10 are shown).
Energy is decomposed into Solvation, None-Polar and Total.
The amino acids making up the P3 pepide sequence are
highlighted in yellow (amino acids 89 to 96 of NSP10).

| Residue | Location | Internal | Solvation | Non-Polar | TOTAL |
|---|---|---|---|---|---|
| LEU | 133 | L | -0.00111 | 0.000527162 | -6.97017 |
| ZN3 | 134 | L | -3.471345 | 1.456503483 | 109.173055 |
| ZN1 | 135 | L | -1.427645 | 0.478173461 | 84.17922 |

Sequences/Variants:
SEQ ID NO: 1 - FMDLKGKY

SEQ ID NO: 2 - YGRKKRRQRRRGSGFMDLKGKY

SEQ ID NO: 3 - RRRRRRRRFMDLKGKY

SEQ ID NO: 4 - CRRRRRRRRCFMDLKGKY

Variant Nucleotide Sequences:
SEQ ID NO. 5 - ccaagtacct ccaccagcat

SEQ ID NO: 6 - gggagttggc cagtaaatca

SEQ ID NO: 7 - cttggagttg gcccatagaa

SEQ ID NO: 8 - tggtgccaca atctgttgtt

SEQ ID NO: 9 - gctcctgctc ctgaaatgac

SEQ ID NO: 10 - ctggagcaat tggtgaggtt

SEQ ID NO: 11 - accaccacta ccaccaccac

SEQ ID NO: 12 - tatccccatt tccaagtcca

SEQ ID NO: 13 - cacgacggag tttcacaaga

SEQ ID NO: 14 - cgatggaagt ttgaggcaat

SEQ ID NO: 15 - YGRKKRRQRRRGSG

SEQ ID NO: 16 - RRRRRRRR

SEQ ID NO: 17 - CRRRRRRRRC

Figure 4:
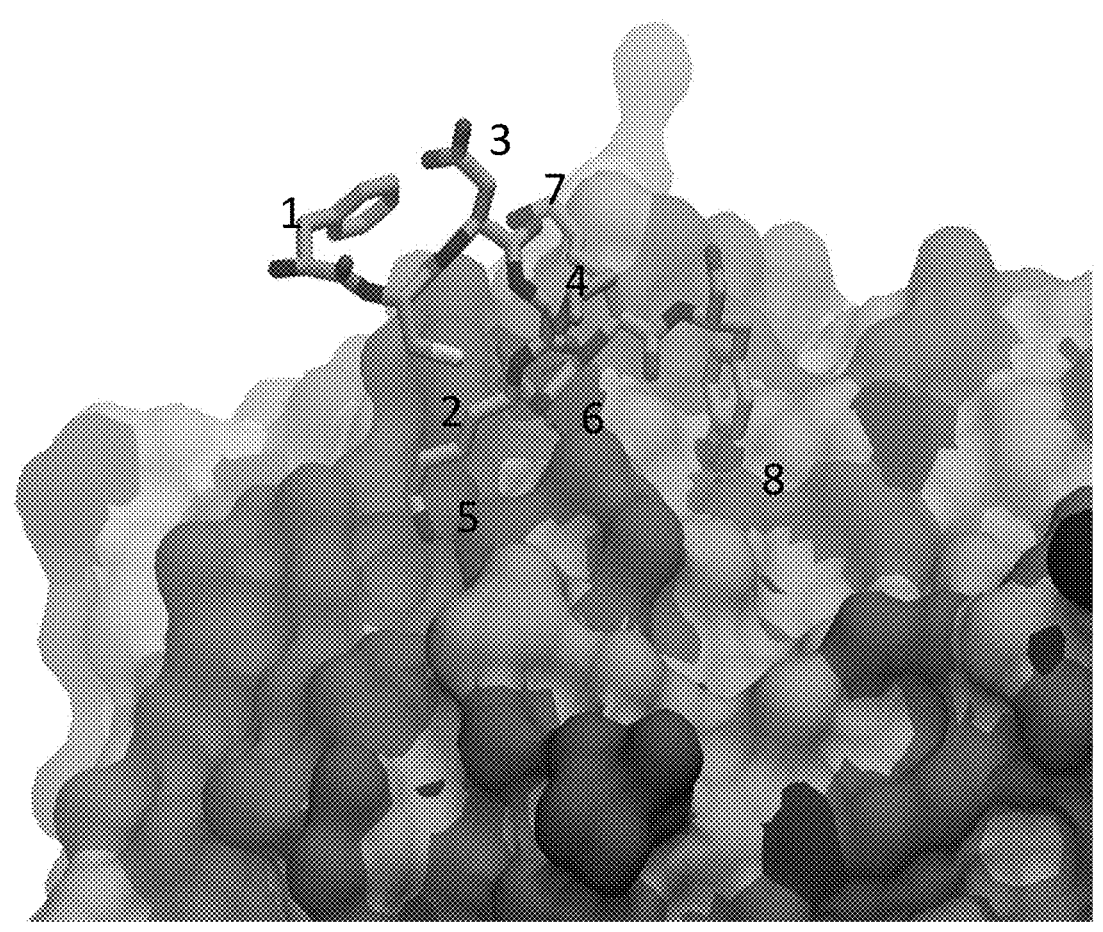
FIG. 4 The structure of the P3 peptide bound to NSP16. Structure is based on the crystal structure (PDB ID: 6W4H) of NSP10/NSP16 complex. Hydrogen bonds are shown as dotted lines. Amino acids of the P3 peptide are shown in the licorice representation as per the Visual molecular Dyanmics (VMD) software. They are numbered from 1 to 8 corresponding to the sequence FMDLKGKY (SEQ ID NO: 1). There are four Hydrogen bonds formed between P3 and the NSP16 protein. The pairs are (written in the format of P3 to NSP16): K5 sidechain to carbonyl carbon of residue S108, G6 amino backbone to sidechain of D109, carbonyl of G6 and sidechain of R89, and phenol sidechain of Y8 to backbone carbonyl of A86.

Additionally, FIG. 4 shows the bound conformation of the peptide inhibitor without the A peptide to NSP16.

The SARS-CoV-2 Methyltransferase enzyme formed by the non-structural protein 10 (NSP10) and non-structural protein 16 (NSP16) is essential for the virus' evasion of host defenses by protecting the viral RNA from interferon response. P1 has high toxicity and stimulates an inflammatory pathway. Using computational methods we developed P3, which we propose could interacts with NSP16.

One of the potential advantages of peptide inhibitors is that resistance is unlikely to arise and that the treatment would likely be effective against emerging strains that evade antibody recognition, hence threatening the efficacy of vaccination.

In a first embodiment of the present disclosure, there is provided a peptide known as P3, according to amino acid sequence FMDLKGKY (SEQ ID NO: 1), wherein the peptide is linked to the HIV Tat peptide sequence to allow penetration of a cellular membrane of a subject, and further comprises a pharmaceutically acceptable carrier for delivery to a subject, wherein the fused amino acid sequence is YGRKKRRQRRRGSGFMDLKGKY (SEQ ID NO: 2).

In a second embodiment, the pharmaceutically acceptable carrier for delivery to a subject can be a nanoparticle, lipid, phospholipid vesicle, polymeric carrier, and phospholipid nanoparticle.

In a third embodiment, the HIV Tat sequence is the 14 amino acid peptide (SEQ ID NO: 15)
YGRKKRRQRRRGSG.

In a second aspect, the invention provides use of the peptides described above, subset of P3, or functional analogues thereof for the production of a pharmaceutical composition for the treatment of a subject suffering or believed to be suffering from a moderate to severe SARS-CoV-2 infection or a related disorder.

In another embodiment, disclosed herein is a pharmaceutical compositions for the treatment of a SARS-CoV-2 infection comprising an effective amount of one or more of the peptides of the present invention, a pharmaceutically acceptable carrier or vehicle for delivery to a subject and one or more pharmaceutical excipients.

In another embodiment, the pharmaceutical composition comprises P3 is linked to the HIV Tat peptide sequence to allow penetration of a cellular membrane of a subject.

In another embodiment, the HIV Tat sequence is the 14 amino acid peptide YGRKKRRQRRRGSG (SEQ ID NO: 15).

In further embodiment, the HIV Tat sequence may be substituted by any other suitable peptide sequences accessible to a person of ordinary skill in the art that allows penetration of the cell membrane.

In a preferred embodiment of the present disclosure, a peptide sequence linked to P3 comprises amino acid sequence YGRKKRRQRRRGSGFMDLKGKY (SEQ ID NO: 2).

In another embodiment, P3 is linked to a shorter sequence of eight Arginine residues (R8), RRRRRRRRFMDLKGKY (SEQ ID NO: 3) or the cyclized equivalent thereof, C*RRRRRRRRC*FMDLKGKY (SEQ ID NO: 4), where C* indicates a cyclized cysteine residue.

In certain embodiments, herein provided is a pharmaceutical composition comprising a therapeutically effective amount of a peptide of sequence P3, comprising a cell-penetrating peptide amino acid sequence, such as from the HIV Tat peptide sequence or the R8 sequence and variations thereof, and a pharmaceutically acceptable carrier for delivery to a subject.

In further embodiments, the HIV Tat peptide sequence comprises the peptide sequence YGRKKRRQRRRGSG (SEQ ID NO: 15) and the R8 sequence comprises RRRRRRRR (SEQ ID NO: 16) or the cyclized variation of R8 (cR8) C*RRRRRRRRC* (SEQ ID NO: 17).

In a third aspect, disclosed is a method of treating a subject afflicted by SARS-CoV-2, the method comprising administering to the subject in need thereof a therapeutically effective amount of the peptide of sequence P3, or a subset thereof, in addition to a cell-penetrating sequence such as shown above, and a pharmaceutically acceptable carrier for delivery to a subject.

In another embodiment, the pharmaceutically acceptable carrier for delivery to a subject can be a nanoparticle, lipid, phospholipid vesicle, polymeric carrier, and phospholipid nanoparticle.

In another embodiment, the subject is a mammal.

In another embodiment, the mammal is a human.

In another embodiment, the subject has a mild to severe SARS-CoV-2 infection.

In preferred embodiments, P3 inhibits the interaction of NSP10/NSP16 preventing Methyltransferase action, thus exposing the viral RNA to Interferon host defenses.

In yet another embodiment, P3 has an Effective Concentration 90% ($EC_{90}$) of 3.3 micromolar against human Caco-2 cells infected with SARS-CoV-2. P3 is not toxic towards Caco-2 cells even at concentrations of 100 g/mL.

Methods of Treatment of SARS-CoV-2 Infection

The above pharmaceutical compositions may be used in novel therapeutic methods of treatment in patients afflicted by SARS-CoV-2 infection. The methods include administering to a subject an effective amount of a pharmaceutical compound composition. In representative embodiments, the subject suffers from SARS-CoV-2 infection. In specific embodiments, the SARS-CoV-2 infection can be symptomatic or none-symptomatic with different degrees of severity.

The above invention can be used to treat SARS-CoV-2 irrespective of the type of strain, and irrespective of the severity associated with the infection, including, but not limited to moderately symptomatic to severely symptomatic can also be treated.

In certain embodiments, the present invention is a pharmaceutical composition comprising the isolated peptides described above for administration to a subject in need thereof. In a particular embodiment according to this embodiment, the pharmaceutical composition of the present invention further comprises a pharmaceutically acceptable carrier. In a related embodiment of the invention, the subject is a mammal, preferably a human.

In another embodiment, antibody drug conjugates (ADC) comprising cysteine engineered antibodies in which one or more amino acids of the wild type or parent antibody are replaced with a cysteine amino acid may be used for targeted delivering of the peptides of the present invention to a subject. Cysteine engineered antibodies are capable of binding (preferably specifically) to an antigen, for example a peptide. Cysteine engineered antibodies can be prepared for conjugation to linker drug intermediates via reduction and reoxidation of intrachain disulfide groups using methods well known in the art. The linker is cleavable in the lysosome that is rich in some proteases, having optimal hydrolytic activity at acidic pH for proper peptide release.

Compositions featuring the aforementioned compounds may be specially formulated for administration in solid or liquid form, including those adapted for the following: (1) oral administration, for example, drenches (aqueous or non-aqueous solutions or suspensions), tablets, e.g., those targeted for buccal, sublingual, and systemic absorption, boluses, powders, granules, pastes for application to the tongue; (2) parenteral administration, for example, by subcutaneous, intramuscular, intravenous or epidural injection as, for example, a sterile solution or suspension, or sustained-release formulation; (3) topical application, for example, as a cream, ointment, or a controlled-release patch or spray applied to the skin; (4) intravaginally or intrarectally, for example, as a pessary, cream or foam; (5) sublingually; (6) ocularly; (7) transdermally; (8) nasally, however it is most likely to be administered intravenously (9)

Wetting agents, emulsifiers and lubricants, such as sodium lauryl sulfate and magnesium stearate, as well as coloring agents, release agents, coating agents, sweetening, flavoring and perfuming agents, preservatives and antioxidants can also be present in the compositions.

Examples of pharmaceutically-acceptable antioxidants include: (1) water soluble antioxidants, such as ascorbic acid, cysteine hydrochloride, sodium bisulfate, sodium metabisulfite, sodium sulfite and the like; (2) oil-soluble antioxidants, such as ascorbyl palmitate, butylated hydroxyanisole (BHA), butylated hydroxytoluene (BHT), lecithin. propyl gallate, alpha-tocopherol, and the like; and (3) metal chelating agents, such as citric acid, ethylenediamine tetraacetic acid (EDTA), sorbitol, tartaric acid, phosphoric acid, and the like.

In certain embodiments, administration of the peptides of the present invention can be formulated and administered to a subject using techniques well known in the art. The peptides can be prepared as acidic or basic salts. Pharmaceutically acceptable salts (in the form of water- or oil-soluble or dispersible products) include conventional non-toxic salts or the quaternary ammonium salts that are formed, e.g., from inorganic or organic acids or bases. Examples of such salts include acid addition salts such as acetate, adipate, alginate, aspartate, benzoate, benzenesulfonate, bisulfate, butyrate, citrate, camphorate, camphorsulfonate, cyclopentanepropionate, digluconate, dodecylsulfate, ethanesulfonate, fumarate, glucoheptanoate, glycerophosphate, hemisulfate, heptanoate, hexanoate, hydrochloride, hydrobromide, hydroiodide, 2-hydroxyethanesulfonate, lactate, maleate, methanesulfonate, 2-naph-thalenesulfonate, nicotinate, oxalate, pamoate, pectinate, persulfate, 3-phenylpropionate, picrate, pivalate, propionate, succinate, tartrate, thiocyanate, tosylate, and undecanoate; and base salts such as ammonium salts, alkali metal salts such as sodium and potassium salts, alkaline earth metal salts such as calcium and magnesium salts, salts with organic bases such as dicyclohexylamine salts, N-methyl-D-glucamine, and salts with amino acids such as arginine and lysine.

In further embodiments, the peptides can be administered using different routes such as an intravenous route, an intraperitoneal route, a subcutaneous route, a topical route, an intramuscular route, or an intranasal route. When administered by injection, the injectable solution or suspension may be formulated using suitable non-toxic, parenterally-acceptable diluents or solvents, such as Ringer's solution or isotonic sodium chloride solution, or suitable dispersing or wetting and suspending agents, such as sterile, bland, fixed oils, including synthetic mono- or diglycerides, and fatty acids, including oleic acid. Pharmaceutically acceptable carriers facilitate storage and administration of a peptide to a patient. Pharmaceutically acceptable carriers may contain different components such as a buffer, sterile water for injection, normal saline or phosphate buffered saline, sucrose, histidine, salts and polysorbate. Regardless of the route of administration selected, the compound may be formulated into pharmaceutically-acceptable dosage forms by conventional methods known to those of skill in the art. The compound may be formulated for administration in any convenient way for use in human or veterinary medicine, by analogy with other pharmaceutical compositions.

In another embodiment, the compositions of the present invention comprise a therapeutically effective amount of a therapeutic agent. The therapeutic amount will vary on the method of administration, condition to be treated, therapeutic agent, and the like. A suitable dosing regimens are preferably determined taking into account factors well known in the art including type of subject being dosed; age, weight, sex and medical condition of the subject; the route of administration; the renal and hepatic function of the subject; the desired effect; and the particular compound employed. Optimal precision in achieving concentrations of drug within the range that yields efficacy without toxicity requires a regimen based on the kinetics of the drug's availability to target sites. This involves a consideration of the distribution, equilibrium, and elimination of a drug. The daily dose for a subject is expected to be between 0.0001 and 1,000 mg per subject per day. The pharmaceutical compositions can be provided in kit. Such a kit typically contains an active compound in dosage forms for administration. A dosage form contains a sufficient amount of active compound such that a beneficial effect can be obtained when administered to a patient during regular intervals, such as 1 to 6 times a day, during the course of 1 or more days. Preferably, a kit contains instructions indicating the use of the dosage form for treating coronavirus and the amount of dosage form to be taken over a specified time period.

In another embodiment, the present invention provides the treatment of a subject suffering or believed to be suffering from disease caused by an infection with the SARS-CoV-2 virus by administration of a pharmaceutical composition comprising a pharmacologically effective amount of the peptides of the present invention or functional analogues thereof together with a pharmaceutically acceptable diluent to said subject. A useful pharmaceutically acceptable diluent is sterile water or an isotonic salt solution such as 0.9% saline or phosphate buffered salt solution (PBS). In a preferred embodiment, the invention provides the treatment of a subject suffering or believed to be suffering from disease caused by an infection with the SARS-CoV-2 virus by administration of a pharmaceutical composition comprising a pharmacologically effective amount of one of the peptide of the present invention or functional analogues thereof together with a pharmaceutically acceptable diluent to said subject. Additionally, a second agent, for example anti-inflammatory, may be administered. The invention thus provides use of a regulatory peptide pharmaceutical composition for application to a subject suffering or believed to be suffering from an infection with the SARS-CoV-2 virus by generating a systemic modulation of the expression of a gene in a cell throughout the body of said subject.

Methods of preparing these formulations or compositions include the step of bringing into association the compound with the carrier and, optionally, one or more accessory ingredients. Usually, the formulations are prepared by uniformly and intimately bringing into association a compound of the present invention with liquid carriers, or finely divided solid carriers, or both, and then, if necessary, shaping the product.

In some embodiments, the present invention relates to compositions for delivery of therapeutic the peptides in cells, and particularly to such compositions for mucosal, oral, nasal, or pulmonary delivery of therapeutic agents. In particular, the present invention comprises carrier particles containing or encapsulating a therapeutic agent or agents, which have been modified on their surface to contain one or more targeting moieties that enable the enhanced uptake and transport of the therapeutic agent via receptor-mediated processes such as endocytosis or transcytosis.

In another embodiment, carrier particles used in the compositions of the present invention can be based on any biologically suitable material and may take a variety of forms, such as biodegradable particles, liposomes, microspheres, nanoparticles, lipids, phospholipid vesicles, polymeric carriers, phospholipid nanoparticles microbubbles, polymersomes, polyplexes, and synthetic secretory granules. All types of materials and structures, including inorganic and organic materials, can be used for the carrier particles of the present invention. Non-limiting examples of these materials and structures include polyesters (such as poly(lactic acid), poly(L-lysine), poly(glycolic acid) and poly(lactic-co-glycolic acid)), poly(lactic acid-co-lysine), poly(lactic acid-graft-lysine), polyanhydrides (such as poly (fatty acid dimer), poly(fumaric acid), poly(sebacic acid), poly(carboxyphenoxy propane), poly(carboxyphenoxy hexane), copolymers of these monomers and the like), poly(anhydride-co-imides), poly(amides), poly(orthoesters), poly(phosphoesters), poly(iminocarbonates), poly(urethanes), poly(phosphazenes), poly(organophosphazenes), poly(phosphates), poly(ethylene vinyl acetate) and other acyl substituted cellulose acetates and derivatives thereof, poly(caprolactone), poly(carbonates), poly(amino acids), poly(acrylates), polyacetals, poly(cyanoacrylates), poly(styrenes), poly(vinyl chloride), poly(vinyl fluoride), poly(vinyl imidazole), chlorosulfonated polyolefins, polyethylene oxide, copolymers, polystyrene, and blends or co-polymers thereof.

In another embodiment, nanoparticles may be formed from compatible polymers and biomaterials such as poly (lactide-co-glycolide) (PLGA), poly(lactide) (PLA), poly F-caprolactone, albumin, and chitosan. The carrier particles may be formed from the biodegradable polymers PLGA or PLA. PLGA and PLA are able to control the release of the therapeutic agents. The carrier particles may otherwise be formed by suitable means known in the art. It is also known in the art how to incorporate or encapsulate one or more therapeutic agents in the carrier particles for delivery.

The carrier particles may be microparticles (about 1-1000 m) or nanoparticles (about 1-1000 nm). In another preferred embodiment, the carrier particles have an average diameter less than about 100 m, about 75 m, about 60 m, about 50 m, about 40 m, about 25 m, about 20 m, about 15 m, about 10 m, about 5 m, about 2.5 m, about 1000 nm (1 m), 500 nm, 300 nm, 200 nm, 150 nm, 100 nm, 75 nm, 50 nm, 30 nm, 20 nm, 15 nm, 10 nm, 5 nm, or 1 nm. In another preferred embodiment, the carrier particles have an average diameter of about 1 nm to about 1 micron, about 5 nm to about 500 nm, about 5 nm to about 200 nm, about 5 nm to about 150 nm, about 5 nm to about 100 nm, about 5 nm to about 75 nm, about 5 nm to about 50 nm, about 10 nm to about 300 nm, about 10 nm to about 200 nm, about 10 nm to about 150 nm, about 10 nm to about 100 nm, about 10 nm to about 75 nm, about 10 nm to about 50 nm, or about 15 nm to about 75 nm.

In another preferred embodiment, the carrier particles have an average diameter greater than about 100 nm, about 200 nm, about 300 nm, about 400 nm, about 500 nm, 600 nm, 700 nm, 800 nm, 900 nm, 950 nm, 1000 nm (1 m), 5 m, 10 m, 15 m, 20 m, 25 m, 40 m, 50 m, 60 m, 75 m or 100 m. In still another preferred embodiment, the carrier particles have an average diameter of about 500 nm to about 500 m, about 600 nm to about 400 m, about 700 nm to about 300 m, about 750 nm to about 250 m, about 800 nm to about 200 m, about 900 nm to about 100 m, about 950 nm to about 50 m, about 975 nm to about 25 m, and about 1000 nm to about 15 m.

The present invention includes pharmaceutical compositions comprising one or more peptides within a pharmaceutically acceptable carrier, and one or more pharmaceutical excipients. The pharmaceutical excipients can be formulated according to known methods for preparing pharmaceutically useful compositions. The excipients may be liquid, solid, or semi-solid, for example. Formulations are described in a number of sources which are well known and readily available to those skilled in the art. Suitable pharmaceutical excipients include starch, glucose, sucrose, gelatin, malt, rice, flour, chalk, silica gel, gluceryl monostearate, talc, sodium chloride, fried skim milk, glycerin, propylene, glycol, water, ethanol, and the like.

In certain embodiments, a formulation of the compound includes an excipient selected from the group consisting of cyclodextrins, liposomes, micelle forming agents, e.g., bile acids, and polymeric carriers, e.g., polyesters and polyanhydrides; and an active ingredient that may be the compound and/or one of its pharmaceutically acceptable derivatives. In certain embodiments, an aforementioned formulation renders orally bioavailable a compound or its derivative. These compositions include, but are not limited to solutions, suspensions, tablets, emulsions, powders and sustained release formulations.

The formulations may be a suppository. Oral formulations may contain substances including but not limited to pharmaceutical grades of mannitol, lactose, starch, magnesium stearate, sodium saccharin, cellulose, and magnesium carbonate. Oral compositions may also include adjuvants such as wetting agents, emulsifying and suspending agents, sweetening, flavoring, coloring, perfuming and preservative agents. Suspensions, in addition to the active compounds, may contain suspending agents as, for example, water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofuryl alcohol, polyethylene glycols and fatty acid esters of sorbitanethoxylated isostearyl alcohols, polyoxyethylene sorbitol and sorbitan esters, microcrystalline cellulose, aluminum metahydroxide, bentonite, agar-agar and tragacanth, and mixtures thereof. Such formulations will contain a therapeutically effective amount of active agent or active agent loaded into the carrier particles, to provide an appropriate mode of administration to a subject in need thereof.

The formulations may conveniently be presented in unit dosage form and may be prepared by any methods well known in the art of pharmacy. The amount of compound which can be combined with a carrier material to produce a single dosage form will vary depending upon the subject being treated, the particular mode of administration. The amount of an active ingredient which can be combined with a carrier material to produce a single dosage form will usually be that amount of the compound which produces a therapeutic effect. Usually, out of one hundred percent, this amount will range from about 1 wt % to about 99 wt % of active ingredient, preferably from about 5 wt % to about 70 wt %, most preferably from about 10 wt % to about 30 wt %.

Additional components of the composition may be chosen from any of those used in or capable of being used in a pharmaceutical formulation. A non-exclusive list of components includes preservatives, stabilizers, chelating agents, dyes, antibiotics, antimicrobials, and anti-fungal agents. for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents which delay absorption such as aluminum monostearate and gelatin.

Suitable techniques for the formulation and administration of the compositions of the present invention are known in the art.

Definitions

As used in this description and the accompanying claims, the following terms shall have the meanings indicated, unless the context otherwise requires:

The phrase "effective amount" indicates the amount of the peptide which is effective to treat any symptom or aspect of SARS-CoV-2 infection. Effective amounts can be determined routinely. Further guidance on dosages and administration regimens is provided below.

The term "treatment" is used conventionally, e.g., the management or care of a subject for the purpose of combating, alleviating, reducing, relieving, improving, etc., one or more of the symptoms associated with SARS-CoV-2 infection and consequences thereof, such as hospitalization time.

Administering effective amounts of the compound can treat one or more aspects of SARS-CoV-2 infection, including, but not limited to, inhibiting viral replication; reducing disease progression; stabilizing the disease; prolonging patient survival; enhancing patient's quality of life; reducing adverse symptoms associated with SARS-CoV-2 infection; and reducing the frequency, severity, intensity, and/or duration of any of the aforementioned aspects.

The term "subject" in accordance with the present invention, includes, e.g., mammals, such as dogs, cats, horses, rats, mice, monkeys, and humans.

As used herein, the term "therapeutically effective amount" means that amount of a peptide, or pharmaceutical agent that will elicit the biological or medical response of a tissue, system, animal or human that is being sought, for instance, by a researcher or clinician. Furthermore, the term "therapeutically effective amount" means any amount which, as compared to a corresponding subject who has not received such amount, results in improved treatment, healing, prevention, or amelioration of a disease, disorder, or side effect, or a decrease in the rate of advancement of a disease or disorder. The term also includes within its scope amounts effective to enhance normal physiological function.

The term "amino acid" as used herein means glycine, alanine, valine, leucine, isoleucine, phenylalanine, proline, serine, threonine, tyrosine, cysteine, methionine, lysine, arginine, histidine, tryptophan, aspartic acid, glutamic acid, asparagine, glutamine or citrulline.

EXPERIMENTAL EXAMPLES

Design of Peptides

Our design starts with previous literature where amino acids 68-96 of NSP10 of MHV, attached to a 14 amino acids HIV's Trans-Activator of Transcription (TAT) protein sequence have been shown to inhibit MHV's replication in cell models and mice animal models [1]. We synthesized the homologous sequence composed of amino acids 68-96 of NSP10 from the SARS-CoV-2 virus, attached the 14 amino acids TAT sequence. We named this peptide P1. P1 is incidentally identical to a peptide used previously to inhibit the NSP10/NSP16 complex formation of SARS-CoV [4]. While previous studies examined P1's effect in cell-free Biochemical assays involving NSP10/NSP16 complex formation and methyltransferase function [4], no proper in vitro study was conducted in which the peptides' effect was examined in cell culture. See FIG. 1 for comparison of sequences of NSP10's interaction region of MHV, SARS-CoV, SARS-CoV-2, and the MERS virus.

The design of peptides P1 and P2 is derived from the SARS-CoV-2's NSP10 protein region that forms the interaction surface with NSP16. We have designed P1 based on homology to the previously-known peptide inhibitors of MHV [1]. P1 constituted sequence completely based on the NSP10's amino acids 68-96 of SARS-CoV-2, while in P2 we attempted to alter the binding capacity by introducing one amino acid substitution, Histidine to Arginine, relying on available X-ray structural data [5]. P1 sequence has ben previously designed to target SARS-CoV's methyltransferase. P1 and P2 peptides were engineered with an N-terminal 14 amino acid sequence corresponding to the protein transduction domain of the HIV's Trans-Activator of Transcription (TAT) protein to allow penetration of the cell membrane. Based on the previous studies, we hypothesized that applying the peptides to SARS-CoV-2-infected cells would inhibit the NSP10/NSP16 complex formation, resulting in a decrease in viral replication. We found that P1, but not P2, exhibited strong cytotoxic activity in intestinal epithelial cells used as viral replication model. Upon application of the peptides in human lung cells a profound induction of IL-6 secretion was observed in the case of P1, but not P2.

Design of Peptide Inhibitors and their Toxicity

In a previous attempt submitted as a recent paper, we designed peptides homologous to the sequences previously shown in literature to target the NSP10/NSP16 interaction of MHV and SARS-CoV [23, 24]. The peptides were conjugated to a 14 amino acid long HIV TAT sequence to allow for cell penetration. FIG. 1 shows the alignment of the sequences derived from NSP10 of SARS-CoV, SARS-CoV-2 and MHV. Sequences of SARS-CoV and SARS-CoV-2 are identical with respect to the NSP10 region of interest, while sequences from MHV and MERS share a Proline to Valine substitution. We designed two peptides (P1 and P2) differing in one amino acid at position 26 (FIG. 2), replacing Histidine with Arginine (H26R) to improve binding based on X-ray structural data. We tested the toxicity of our P1 and P2 against Caco-2 cells, routinely used in studies to examine potential drugs against SARS-CoV-2 due to viral preference for replication [26]. We determined that while P2 had no detectable toxicity at concentrations up to 100 g/mL, P1 displayed a Cytotoxic Concentration ($CC_{50}$) of 11 g/mL.

SARS-CoV-2 NSP10-Derived Sequences Cause an Increase in IL-6 in Human Lung Cells We measured the levels of IL-6 in a PBS control, with P1 pre-treatment, P2 pre-treatment, and a P3 sequence pre-treatment. As shown in FIG. 3, stimulation of the human NSCLC cell line H1792 with P1, but not P2 nor P3, resulted in a more than 4-fold stimulation of the intrinsic secretion of IL-6. The TAT sequence was also tested and showed no increase in IL-6.

The sequence of P1 and P2 both contain a Zinc coordinated by three Cysteines and a Histidine residue. This domain is part of the NSP10 structure. Such domains are indeed known to correlate with activation of IL-6. In osteoarthiritic mice, the suppression of proteins containing this domain correlated with the reduction in IL-6 expression [27]

In designing P3, we have used MM-PBSA simulations to find the amino acids most likely to contribute to the binding of the peptide to NSP16. We used the entire sequence of NSP10 and found eight amino acids that are part of the P1 and P2 sequence but do not contain the Zinc knuckle motif. Table 1 shows the raw data indicating decomposition of the binding energy between NSP10 and NSP16 based on the MM-PBSA simulation. We have then tested the peptide P3 for stimulation of IL-6 (FIG. 3). Once it was found that it does not stimulate IL-6, we have then tested the peptide in Caco-2 cells infected with SARS-CoV-2, P3 has a 90% Effective Concentration ($EC_{90}$) of 3.3 PM. It also has no detectable cytotoxicity even at 100 g/mL.

Material and Methods

Design of the Peptides

The peptides were designed by using the sequence of NSP10 in SARS-CoV-2 that is homologous to MHV's NSP10 region interacting with NSP16 as this was the aim of inhibition. The HIV-Tat peptide sequence (YGRKKRRQRRRGSG) (SEQ ID NO: 15) was added to the N-terminus. The peptides were modified with N-acetylation and C-amidation, artificially synthesized, purified using High Performance Liquid Chromatography (HPLC) and ensured not to have any disulfide bonds using Mass Spectrometry (MS) (Peptides 2.0 Inc). Prior to use, peptides were dissolved in 1×PBS.

Toxicity Tests of the Peptides for Caco-2 Cells Infected with SARS-CoV-2 Virus

Testing for toxicity of the peptides against cells infected with SARS-CoV-2 was done in a BSL-3 facility at Utah State University, part of the NIH/NIAID program. Confluent or near-confluent cell culture monolayers of Caco-2 cells were prepared in 96-well disposable microplates the day before testing. Cells were maintained in MEM supplemented with 5% FBS. The peptides were dissolved in 1×PBS and concentrations of 0.1, 1.0, 10, 100, and 200 g/mL were prepared. Five microwells were used per dilution: three for infected cultures and two for uninfected toxicity cultures. On every plate controls for the experiment consisted of six microwells that were infected but not treated (virus controls) and six that were untreated and uninfected (cell controls). P1, P2, and P3 were tested in parallel with a positive control drug using the same method as was applied for the peptides. The positive control was included with every test run. Growth media were removed and the peptides (0.1 mL) were applied to the wells at 2× concentration. Aliquots (0.1 mL), containing virus at ~60 CCID50 (50% cell culture infectious dose) were added to the wells designated for virus infection. Media devoid of virus was added to the toxicity control wells and cell control wells. Plates were incubated at 37° C. with 5% CO2 until marked CPE (>80% CPE for most virus strains) was observed in virus control wells. The plates were then stained with 0.011% neutral red for two hours at 37 degrees Celsius in a 5% CO2 incubator. The neutral red medium was removed by complete aspiration, and the cells were rinsed 1× with PBS to remove residual dye. The PBS was completely removed, and the incorporated neutral red was eluted with 50% Sorensen's citrate buffer/50% ethanol for at least 30 minutes. The dye content in each well was quantified using a microplate reader at 540 nm. The dye content in each set of wells was converted to a percentage of dye present in untreated control wells using a Microsoft Excel computer-based spreadsheet and normalized based on the virus control. The 50% effective (EC50, virus-inhibitory) concentrations and 50% cytotoxic (CC50, cell-inhibitory) concentrations were then calculated by regression analysis. It was not possible for us to compute the 50% effective (EC50, virus-inhibitory) since Peptide 1 was too toxic at 11 μg/mL while Peptide 2 had no detectable effect against the virus-infected cells even at 100 g/mL concentration, albeit being non-toxic at that concentration.

REFERENCES

[1] Hu, B.; Guo, H.; Zhou, P.; Shi, Z. L. Nature Reviews Microbiology. 2020.

[2] Pedersen, S. F.; Ho, Y. C. J. Clin. Invest. 2020.

[3] Tang, D.; Comish, P.; Kang, R. PLoS Pathogens. 2020.

[4] Tian, S.; Hu, W.; Niu, L.; Liu, H.; Xu, H.; Xiao, S. Y. J. Thorac. Oncol. 2020.

[5] Krafcikova, P.; Silhan, J.; Nencka, R.; Boura, E. Nat. Commun. 2020.

[6] Conti, P.; Ronconi, G.; Caraffa, A.; Gallenga, C. E.; Ross, R.; Frydas, I.; Kritas, S. K. J Biol Regul Homeost Agents 2020.

[7] Liu, T.; Zhang, J.; Yang, Y.; Ma, H.; Li, Z.; Zhang, J.; Cheng, J.; Zhang, X.; Zhao, Y.; Xia, Z.; Zhang, L.; Wu, G.; Yi, J. medRxiv. 2020.

[8] Chen, G.; Wu, D.; Guo, W.; Cao, Y.; Huang, D.; Wang, H.; Wang, T.; Zhang, X.; Chen, H.; Yu, H.; Zhang, X.; Zhang, M.; Wu, S.; Song, J.; Chen, T.; Han, M.; Li, S.; Luo, X.; Zhao, J.; Ning, Q. J. Clin. Invest. 2020.

[9] Scheller, J.; Chalaris, A.; Schmidt-Arras, D.; Rose-John, S. Biochimica et Biophysica Acta—Molecular Cell Research. 2011.

[10] Cronkite, D. A.; Strutt, T. M. J. Immunol. Res. 2018.

[11] Mantovani, A.; Dinarello, C. A.; Molgora, M.; Garlanda, C. Immunity. 2019.

[12] Nold, M. F.; Nold-Petry, C. A.; Zepp, J. A.; Palmer, B. E.; Bufler, P.; Dinarello, C. A. Nat. Immunol. 2010.

[13] Lin, H.; Ho, A. S.; Haley-Vicente, D.; Zhang, J.; Bernal-Fussell, J.; Pace, A. M.; Hansen, D.; Schweighofer, K.; Mize, N. K.; Ford, J. E. J. Biol. Chem. 2001.

[14] Mei, Y.; Liu, H. Cancer Reports. 2019.

[15] Allam, G.; Gaber, A. M.; Othman, S. I.; Abdel-Moneim, A. Int. Rev. Immunol. 2020.

[16] Yang, Z.; Kang, L.; Wang, Y.; Xiang, J.; Wu, Q.; Xu, C.; Zhou, Y.; Chen, S.; Fang, H.; Liu, J.; Dong, M. Canadian Journal of Cardiology. 2019.

[17] Ummarino, D. Nat. Rev. Rheumatol. 2017.

[18] Xu, W. D.; Huang, A. F. Frontiers in Immunology. 2018.

[19] Xie, L.; Huang, Z.; Li, H.; Liu, X.; Zheng, S.; Su, W. Biomolecules. 2019.

[20] Conti, P.; Caraffa, A.; Gallenga, C. E.; Ross, R.; Kritas, S. K.; Frydas, I.; Younes, A.; Ronconi, G. J. Biol. Regul. Homeost. Agents 2020.

[21] Li, A.; Ling, Y.; Song, Z.; Cheng, X.; Ding, L.; Jiang, R.; Fu, W.; Liu, Y.; Hu, H.; Yuan, S.; Chen, J.; Zhu, C.; Fan, J.; Wang, J.; Jin, Y.; Zhang, M.; Zhu, L.; Sun, P.; Zhang, L.; Qin, R.; Zhang, W.; Qiu, C.; Shen, Y.; Zhang, L.; Shi, Z.; Zhao, C.; Zhu, T.; Lu, H.; Zhang, X.; Xu, J. J. Infect. Dis. 2020.

[22] Masiá, M.; Fernández-González, M.; Padilla, S.; Ortega, P.; García, J. A.; Agulló, V.; García-Abellán, J.; Telenti, G.; Guillén, L.; Gutiérrez, F. EBioMedicine 2020.

[23] Wang, Y.; Sun, Y.; Wu, A.; Xu, S.; Pan, R.; Zeng, C.; Jin, X.; Ge, X.; Shi, Z.; Ahola, T.; Chen, Y.; Guo, D. J. Virol. 2015.

[24] Ke, M.; Chen, Y.; Wu, A.; Sun, Y.; Su, C.; Wu, H.; Jin, X.; Tao, J.; Wang, Y.; Ma, X.; Pan, J. A.; Guo, D. Virus Res. 2012.

[25] Gordon, D.; Jang, G.; Bouhaddou, M.; Xu, J.; Obernier, K.; O'Meara, M.; Guo, J.; Swaney, D.; Tummino, T.; Huttenhain, R.; Kaake, R.; Richards, A.; Tutuncuoglu, B.; Foussard, H.; Batra, J.; Haas, K.; Modak, M.; Kim, M.; Haas, P.; Polacco, B.; Braberg, H.; Fabius, J.; Eckhardt, M.; Soucheray, M.; Bennett, M.; Cakir, M.; McGregor, M.; Li, Q.; Naing, Z. Z. C.; Zhou, Y.; Peng, S.; Kirby, I.; Melnyk, J.; Chorba, J.; Lou, K.; Dai, S.; Shen, W.; Shi, Y.; Zhang, Z.; Barrio-Hernandez, I.; Memon, D.; Hernandez-Armenta, C.; Mathy, C.; Perica, T.; Pilla, K.; Ganesan, S.; Saltzberg, D.; Ramachandran, R.; Liu, X.; Rosenthal, S.; Calviello, L.; Venkataramanan, S.; Lin, Y.; Wankowicz, S.; Bohn, M.; Trenker, R.; Young, J.; Cavero, D.; Hiatt, J.; Roth, T.; Rathore, U.; Subramanian, A.; Noack, J.; Hubert, M.; Roesch, F.; Vallet, T.; Meyer, B.; White, K.; Miorin, L.; Agard, D.; Emerman, M.; Ruggero, D.; Garcia-Sastre, A.; Jura, N.; Zastrow, M. von; Taunton, J.; Schwartz, O.; Vignuzzi, M.; d'Enfert, C.; Mukherjee, S.; Jacobson, M.; Malik, H.; Fujimori, D.; Ideker, T.; Craik, C.; Floor, S.; Fraser, J.; Gross, J.; Sali, A.; Kortemme, T.; Beltrao, P.; Shokat, K.; Shoichet, B.; Krogan, N. Nature 2020.

[26] Cagno, V. The Lancet Microbe 2020.

[27] Ansari, M. Y.; Khan, N. M.; Ahmad, N.; Green, J.; Novak, K.; Haqqi, T. M. Arthritis Rheumatol. 2019.

[28] Li, J.; Guo, M.; Tian, X.; Wang, X.; Yang, X.; Wu, P.; Liu, C.; Xiao, Z.; Qu, Y.; Yin, Y.; Wang, C.; Zhang, Y.; Zhu, Z.; Liu, Z.; Peng, C.; Zhu, T.; Liang, Q. Med 2021.

[29] Nyati, K. K.; Masuda, K.; Mahabub-Uz Zaman, M.; Dubey, P. K.; Millrine, D.; Chalise, J. P.; Higa, M.; Li, S.; Standley, D. M.; Saito, K.; Hanieh, H.; Kishimoto, T. Nucleic Acids Res. 2017.

[30] Brandio, S. C. S.; Ramos, J. de O. X.; Dompieri, L. T.; Godoi, E. T. A. M.; Figueiredo, J. L.; Sarinho, E. S. C.; Chelvanambi, S.; Aikawa, M. Cytokine and Growth Factor Reviews. 2020.

[31] Totura, A. L.; Whitmore, A.; Agnihothram, S.; Schafer, A.; Katze, M. G.; Heise, M. T.; Baric, R. S. MBio 2015.

[32] Van De Veerdonk, F. L.; Stoeckman, A. K.; Wu, G.; Boeckermann, A. N.; Azam, T.; Netea, M. G.; Joosten, L. A. B.; Van Der Meer, J. W. M.; Hao, R.; Kalabokis, V.; Dinarello, C. A. Proc. Natl. Acad. Sci. U.S.A 2012.

[33] Mora, J.; Schlemmer, A.; Wittig, I.; Richter, F.; Putyr-ski, M.; Frank, A. C.; Han, Y.; Jung, M.; Ernst, A.; Weigert, A.; BrUne, B. J. Mol. Cell Biol. 2016.

[34] Yuan, X. L.; Li, Y.; Pan, X. H.; Zhou, M.; Gao, Q. Y.; Li, M. C. Mol. Biol. (Mosk). 2016.

[35] Yu, H.; Liu, Y.; Xie, W.; Xie, Q.; Liu, Q.; Cheng, L. Int. Immunopharmacol. 2020.

[36] Bulau, A. M.; Nold, M. F.; Li, S.; Nold-Petry, C. A.; Fink, M.; Mansell, A.; Schwerd, T.; Hong, J.; Rubartelli, A.; Dinarello, C. A.; Bufler, P. Proc. Natl. Acad. Sci. U.S.A 2014.

[37] Sharma, S.; Kulk, N.; Nold, M. F.; Graf, R.; Kim, S. H.; Reinhardt, D.; Dinarello, C. A.; Bufler, P. J. Immunol. 2008.

What is claimed is:

1. A peptide consisting of the amino acid sequence YGRKKRRQRRRGSGFMDLKGKY (SEQ ID NO: 2), wherein the peptide reduces replication of severe acute respiratory syndrome coronavirus 2 (SARS-CoV-2) in a subject in need thereof.

2. A pharmaceutical composition comprising the peptide according to claim 1 and a pharmaceutically acceptable carrier for delivery to the subject.

3. The composition of claim 2, wherein the pharmaceutically acceptable carrier for delivery to a subject is selected from the group consisting of: nanoparticles, lipids, phospholipid vesicles, polymeric carriers, and phospholipid nanoparticles.

4. The pharmaceutical composition of claim 2, wherein the subject is a mammal.

5. The pharmaceutical composition of claim 4, wherein the mammal is a human.

6. The peptide of claim 1, wherein the subject is a mammal.

7. The peptide of claim 6, wherein the mammal is a human.

8. A method of treating a subject infected with SARS-CoV-2, wherein the method comprises administering to the subject a therapeutically effective amount of the pharmaceutical composition of claim 2.

9. The method of claim 8, wherein the subject is a mammal.

10. The method of claim 9, wherein the mammal is a human.

11. The method of claim 10, wherein the subject has a mild to severe SARS-CoV-2 infection.

12. The method of claim 8, wherein the pharmaceutical composition further comprises one or more pharmaceutical excipients.

* * * * *